(12) United States Patent
Schwartz et al.

(10) Patent No.: US 8,221,973 B2
(45) Date of Patent: Jul. 17, 2012

(54) METHODS OF WHOLE GENOME ANALYSIS

(75) Inventors: David C. Schwartz, Madison, WI (US);
Konstantinos D. Potamousis, Madison, WI (US); Shiguo Zhou, Madison, WI (US); Steven J. Goldstein, Madison, WI (US); Michael A. Newton, Madison, WI (US); Rodney A. Runnheim, Madison, WI (US); Daniel K. Forrest, Fitchburg, WI (US); Christopher P. Churas, La Jolla, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 455 days.

(21) Appl. No.: 12/253,625

(22) Filed: Oct. 17, 2008

(65) Prior Publication Data

US 2009/0104611 A1    Apr. 23, 2009

Related U.S. Application Data

(60) Provisional application No. 60/980,639, filed on Oct. 17, 2007.

(51) Int. Cl.
*C12Q 1/68* (2006.01)
(52) U.S. Cl. ...................................... 435/6.1
(58) Field of Classification Search ........................ None
See application file for complete search history.

(56) References Cited

FOREIGN PATENT DOCUMENTS

| WO | 02/101095 A1 | 12/2002 |
| WO | WO02/101095 | * 12/2002 |
| WO | 2007/065025 A2 | 6/2007 |

OTHER PUBLICATIONS

Morgan et al. (Biological Chemistry, 2000, vol. 381, p. 1123-1125).*
Didier et al. (J. Neuroscience, 16(7):2238-2250).*
Gorczyca et al. (Cancer Research, 1993, 53:1945-1951).*
Lee et al. (Nucleic Acids Research, 1992, 20(10):2471-2483).*
Ananieve, Gene E. et al., "Optical mapping discerns genome wide DNA methylation profiles," BMC Molecular Biology, Biomed Central Ltd, GB, vol. 9, No. 1, p. 68 (Jul. 30, 2008).
Anantharaman, Thomas et al., "Genomics via Optical Mapping III: Contiging Genomic DNA and Variations," Courant Institute, NY University, pp. 1-12, Oct. 1997.
Antoniotti, M. et al., "Genomics via Optical Mapping IV: Sequence Validation via Optical Map Matching," Internet Citation [online] XP002433390 Retrieved from the Internet: URL:http://citeseer.ist.psu.edu/cache/papers/cs/20815/http:zSzzSzwww.cs.nyu.eduzSzcswebzSzResearchzSzTechReportszSz TR2000-811zSzTR2000-811.pdf/antoniotti01genomics.pdf.
Aston, C. et al., "Optical mapping and its potential for large-scale sequencing projects," Trends in Biotechnology, Elsevier Publications, Cambridge, GB, vol. 17, No. 7, pp. 297-302 (Jul. 1, 1999).
Bousse, L. et al., "Electrokinetically controlled microfiuidic analysis systems," Annu. Rev. Biophys, Biomol Struct. 29:155-181 (2000).
Goesmann, A. et al., "PathFinder: reconstruction and dynamic visualization of metabolic pathways," Bioinformatics vol. 18 No. 1, pp. 124-129 (2002).
Heiter, D. et al., "Site-specific DNA-nicking mutants of the heterodimeric restriction endonuclease R. BbvCI," J. Mol. Biol. 348:631-640 (2005).
Jing, J. et al., "Automated High Resolution Optical Mapping Using Arrayed, Fluid-Fixed DNA Molecules," Proceedings of the National Academy of Sciences of USA, National Academy of Science, Washington, DC., US, vol. 95, pp. 8046-8051 (Jul. 1, 1998).
Ramanathan, A. et al., "An integrative approach for the optical sequencing of single DNA molecules," Analytical Bichoemistry, Academic Press Inc. NY, vol. 330, No. 2, pp. 227-241 (Jul. 15, 2004).
Rye, H. et al., "Stable fluorescent dye-DNA complexes in high sensitivity detection of protein-DNA interactions. Application to heat shock transcription factor," J. Biol. Chem. 268:25229-25238 (1993).
Wabuyele, B. et al., "Single molecule detection of double-stranded DNA in poly(methylmethacrylate) and polycarbonate microfluidic devices," Electrophoresis 22:3939-3948 (2001).
Zhou, S. et al., "Single-Molecule Approach to Bacterial Genomic Comparisons via Optical Mapping," Journal of Bacteriology, pp. 7773-7782, (Nov. 2004).

* cited by examiner

*Primary Examiner* — Stephanie K Mummert
(74) *Attorney, Agent, or Firm* — Quarles & Brady LLP

(57) ABSTRACT

Methods are provided for ascertaining the sequence of a genomic DNA sample by nicking the DNA sample with a restriction nicking enzyme, followed by nick translation with labeled nucleotides, such that the labeled nucleotides can be quantified and compared to a known, reference genome.

32 Claims, 1 Drawing Sheet

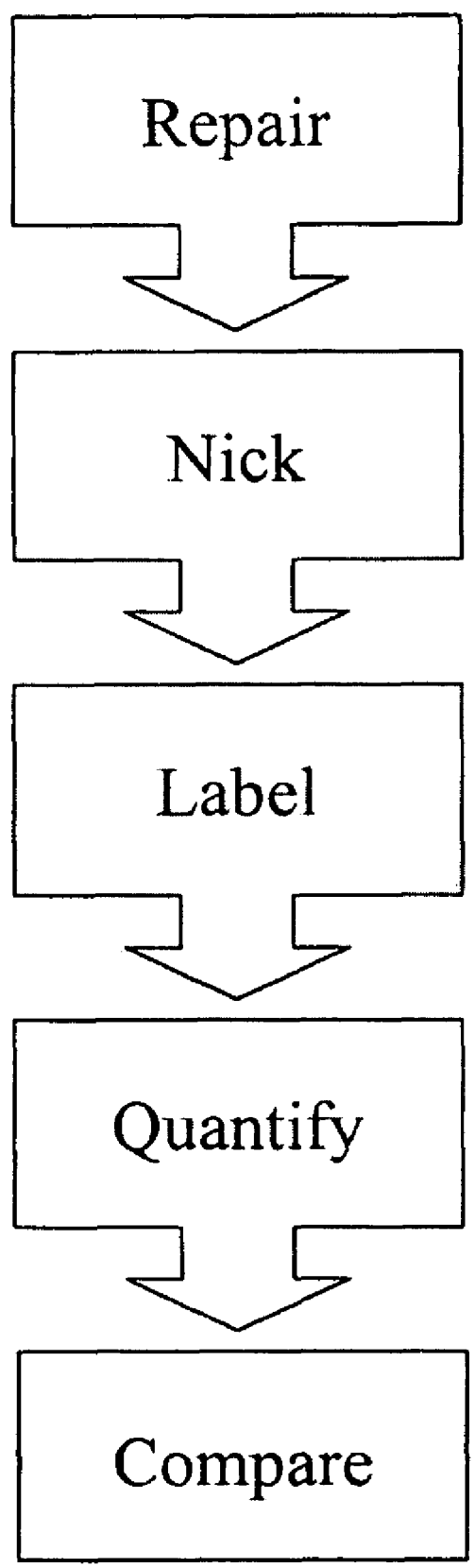

METHODS OF WHOLE GENOME ANALYSIS

CROSS-REFERENCE TO RELATED APPLICATIONS

The application claims the benefit of U.S. Provisional Application No. 60/980,639 filed on Oct. 17, 2007. This application is incorporated herein by reference as if set forth in its entirety.

STATEMENT REGARDING FEDERALLY SPONSORED RESEARCH OR DEVELOPMENT

This invention was made with United States government support awarded by the following agency: NIH RO1 HG000225. The United States government has certain rights in this invention.

BACKGROUND

The invention relates generally to methods of whole genome analysis, and more particularly relates to methods for ascertaining information about the nucleotide composition of a region of a DNA molecule bounded by a nick site and a termination site. The ascertained nucleotide composition can be compared to nucleotide composition data from a reference genome so that differences, if any, from a comparable region of the reference genome can be identified without the need to re-sequence the region.

The human genome harbors many types of genetic aberrations, such as polymorphisms expressed at a single nucleotide and structural level, as well as large-scale events, particularly those associated with cancer. Some aberrations, such as single nucleotide polymorphisms (SNPs), involve only a single nucleotide and may fall within exons or introns of genes, or within the heterochromatic regions between genes. SNPs within a coding sequence do not necessarily change the amino acid sequence of a protein encoded by a gene, due to degeneracy of the genetic code. However, because SNPs are mutations in DNA, they serve as markers for disease and for nucleotide position. In addition, SNPs located in heterochromatic regions between genes may still have consequences for gene splicing or transcription factor binding.

Other genetic aberrations involve more than single nucleotides and can therefore affect intermediate structure of DNA. Examples of these genetic aberrations include, but are not limited to, amplifications, insertions, deletions, inversions and rearrangements. Typically, these aberrations are analyzed with classical cytogenetics and, more recently, using data acquired from high-density, oligonucleotide arrays.

However, there is a continuing need for rapid, simple, comprehensive and cost-effective methods of whole genome analysis that leverage, or complement, emerging sequencing systems.

BRIEF SUMMARY

In a first aspect, a method for acquiring sequence composition information from a DNA molecule includes the steps of introducing a sequence-specific, single-stranded nick site into the molecule, incorporating labeled nucleotides into a region of DNA extending from the nick site to a termination site, quantifying the incorporated nucleotides in the region to ascertain its nucleotide composition, and comparing the ascertained nucleotide composition to nucleotide composition data from a reference genome to determine whether the composition of the region is the same as or different from that of the reference genome.

The nucleotide sequence in the region between the nick site and the termination site determines the number of labeled nucleotides, and thus the amount of label, incorporated during the incorporation step. A difference in amount of label incorporated in the region relative to the amount expected from the reference genome sequence indicates that the genomic DNA differs from the reference sequence in the region.

In some embodiments of the first aspect, the method further includes the step of tagging the DNA molecule at one or more locations outside the region labeled in the method. In other embodiments of the first aspect, the method optionally includes the step of reducing or preventing incorporation of label from non-sequence-specific, endogenous nick sites in the DNA molecule in the label-incorporating step. Endogenous nick sites can be repaired (ligated) or blocked before carrying out the label-incorporating step. In still other embodiments of the first aspect, the method optionally includes the step of removing protein from the DNA (i.e., remove histones or any other native proteins that may bind to DNA, especially genomic DNA).

The described embodiments have many advantages, including permitting analysis of genomic DNA with a simple preparation and yielding sequence information having a resolution approaching that of re-sequencing. The methods permit acquisition of sequence information from heterochromatic regions, pinpoints structural variants in genomes and characterizes aberrations associated with cancer genomes. Likewise, the methods generate a treated DNA molecule, by virtue of having a series of mapped fluorescent punctuates, that provides information allowing for its identification even prior to its alignment to the reference genome. Furthermore, the methods permit all biochemical steps to take place within one reaction chamber (i.e., biochemical steps are not performed on a surface or within such a device) and without the need for cycles of biochemical steps.

These and other features, aspects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 1 shows one embodiment of the basic sequencing scheme, which involves using a nicking restriction enzyme to introduce a nick site followed by incorporation of labeled nucleotides via nick translation to a termination site.

While the present invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents and alternatives falling within the spirit and scope of the invention as defined by the appended claims.

DESCRIPTION OF PREFERRED EMBODIMENTS

DNA molecules, especially genomic DNA molecules, can be unraveled and elongated in a low ionic strength buffer because persistence length of DNA molecules inversely varies with ionic strength of a buffer. See US Published Patent Application No. 2007/0161028, incorporated herein by reference as if set forth in its entirety. Additional methods of unraveling DNA are generally known to those of ordinary skill in the art. See, e.g., Schwartz D & Koval M, "Conformational dynamics of individual DNA molecules during gel electrophoresis," Nature 338:520-522 (1989); Guo X, et al., "Sizing single DNA molecules," Nature 359:783-784 (1992); Schwartz D, et al., "Ordered restriction maps of *Saccharomyces cerevisiae* chromosomes constructed by optical mapping," Science 262:110-114 (1993); Wang Y & Schwartz D, "Sequence-specific cleavage techniques," U.S. Biochem. 20:89-93 (1994); Cai W, et al., "Ordered restriction endonuclease maps of yeast artificial chromosomes created by optical mapping on surfaces. Proc. Natl. Acad. Sci. USA 92:5.164-5168 (1995); Meng X et al., "Optical Mapping of lambda bacteriophage clones using restriction endonucleases," Nature Genetics 9:432-438 (1995); Morozov V, et al., "New polyacrylamide gel-based methods of sample preparation for optical microscopy: immobilization of DNA molecules for optical mapping," J. Microscopy 183:205-214 (1996); and Schwartz D & Samad A, "Optical mapping approaches to molecular genomics," Curr. Opin. Biotechnol. 8:70-74 (1997); Dimalanta E, et al., "A microfluidic system for large DNA molecule arrays," Anal. Chem. 76:5293-5301 (2004), each of which is incorporated herein by reference as if set forth its entirety.

A sequence-specific nick is introduced at a site on one strand of an unraveled DNA molecule. The DNA molecule can be a DNA molecule from any source, e.g., a genomic DNA molecule, a PCR amplicon or a clone. The nick site can be introduced by cleaving the molecule with a nicking restriction enzyme, a natural or engineered endonuclease that catalyzes single strand, but not double strand, DNA cleavage. Nicking restriction enzymes include, but are not limited to, Nb.BsmI, Nb.BsrDI, Nb.BtsI, Nb.BbvCI, Nt.AlwI, Nt.BbvCI, Nt.BstNBI, Nt.SapI or Nt.CviPII. Other known nicking restriction enzymes are believed compatible with the described methods. In addition, known methods for converting double-strand-cleaving restriction enzymes into single-strand-nicking restriction enzymes can be used to generate enzymes suitable for use with the described methods. See, e.g., U.S. Pat. Nos. 6,395,523; 7,081,358; and US Published Patent Application No. 2005/0158834, each of which is incorporated herein by reference as if set forth in its entirety. Other methods for introducing single-strand nicks into DNA can also be used in the described methods, including, DNAse digestion, UV irradiation, HinPI, gamma irradiation and Fenton reactions involving iron ($Fe^{2+}$) and hydrogen peroxide ($H_2O_2$). See, e.g., D'Andrea A & Haseltine W, "Sequence specific cleavage of DNA by the antitumor antibiotics neocarzinostatin and bleomycin," PNAS 75:3608-3612 (1978); Horton J, et al., "DNA nicking by HinPII endonuclease: bending, base flipping and minor groove expansion," Nucleic Acids Res. 34:939-948 (2006) and U.S. Pat. No. 6,306,596, each of which is incorporated herein by reference as if set forth in its entirety.

Labeled nucleotides can be introduced by any technique known to one of ordinary skill in the art, such as a polymerase. For example, one could use a Klenow fragment or phi29 DNA polymerase in a strand displacement reaction to introduce labeled nucleotides. Alternatively, one could use T7 exonuclease in a gap filling reaction to introduce labeled nucleotides. Alternatively still, one could use pre-labeled oligonucleotides in a gap filling reaction to introduce labeled nucleotides. In fact, a given oligonucleotide could be labeled with a single fluorochrome or with additional fluorochromes to increase signal. Moreover, one could use nick translation to introduce labeled nucleotides.

In nick translation, labeled nucleotides are introduced during a reaction from a nick site and extend from the nick site to a termination site. The labeled region is sometimes referred to herein as a 'neighborhood.' If information about the content of more than one nucleotide in the region downstream of the nick site is desired, then a plurality of separate nick translation reactions can be performed, wherein each reaction includes one labeled nucleotide (A, C, G or T). The nucleotides can be labeled with, e.g., fluorochromes, such as Alexa Fluor-labeled nucleotides. Alternatively, the nucleotides can be modified to incorporate moieties that support conjugation of observable labels post-incorporation, e.g., thiolated nucleotides or α-S nucleotide triphospate could directly bind gold nanoparticles or gold nanocrystals. See, e.g., U.S. Pat. No. 6,979,729; Gelles J, et al., "Tracking kinesin-driven movements with nanometre-scale precision," Nature 331:450-453 (1998), each of which is incorporated herein by reference as if set forth in its entirety. Likewise, quantum dots, crystals and particles can also be used.

The nick translation step proceeds until two labeled nucleotides are incorporated; it is believed that the consecutively labeled nucleotides provide steric hindrance between the nucleotides and a polymerase. See Ramanathan A, et al., "High density polymerase-mediated incorporation of fluorochrome-labeled nucleotides," Anal. Biochem. 337:1-11 (2005); and Ramanathan A, et al., "An integrative approach for the Optical Sequencing of single DNA molecules," Anal. Biochem. 330:227-241 (2004), each of which is incorporated herein by reference as if set forth in its entirety. Thus, the polymerase used affects the number of nucleotides added before nick translation is terminated. For example, phi29 polymerase incorporates three labeled nucleotides before terminating nick translation. In an alternative embodiment of the method, the nick translation step can terminate upon incorporation of a ddNTP (i.e., having one of the four nucleotides solely a ddNTP).

The nick site and the termination site define start and end points of a region of the DNA molecule (i.e., the neighborhood). The amount of label incorporated into the region depends upon the sequence of the labeled region. Accordingly, each region has a unique signature characterized by a quantifiable number of labeled nucleotides in the region. The nucleotide content in the region is obtained by comparing the amount of label incorporated in the region to the expected amount in the comparable region of a reference genome having a known sequence. For example, if the region is nick translated using labeled dATP, the quantum of label measured is proportional to the number of incorporated A's. Likewise, if the region is nick translated using labeled dCTP, the quantum of label measured is proportional the number of incorporated C's. The length of the region labeled in each label-incorporating step will depend upon when the sequence of the molecule includes at least two consecutive incorporations of the selected labeled nucleotide. If four separate labeling reactions are conducted, one can ascertain the complete nucleotide composition of the labeled region, which provides information content approaching that of re-sequencing. However, it is also contemplated that one of ordinary skill in the art could use multiplexing with differentially labeled nucleotides, which would allow for a single reaction.

Optionally, one of ordinary skill in the art can increase the specificity of the nick translation step by repairing or blocking endogenous nicks in the DNA sample before introducing the sequence-specific nick, as described herein. DNA ligase can be used to remove endogenous nicks from the DNA. In addition, nicks can be blocked by incorporating ddNTPs through nick translation or through strand displacement. Likewise, one can globally tag the DNA sample with a labeled molecule outside the region labeled to enhance visualization of labeled nucleotides in the region. For example, the DNA backbone can be stained with YOYO-1 or any other suitable DNA stain, including, but not limited to, DAPI, TOTO, ethidium bromide or propidium bromide. Also, protein can be removed from the genomic DNA sample. These and other steps can be taken to clean up the DNA before the labels are quantified. As such, one can remove cellular proteins, unincorporated fluorochromes or enzymes from the reaction.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein.

The invention will be more fully understood upon consideration of the following non-limiting Examples.

EXAMPLES

Example 1

Processing of "Raw" Genomic DNA for Sequence Acquisition

The methods described herein for preparing linear or linearized genomic DNA molecules (although any DNA molecule can be used) simplify marking of DNA molecules with multiple fluorescent labels. The use of fluorescence resonance energy transfer (FRET), in which one fluorescent material (i.e., donor, such as YOYO-1) produces light that excites the other (i.e., acceptor, such as fluorochrome-labeled nucleotides), allows dual color imaging and reduces the effects of unincorporated dyes because of a limited range of this effect. As noted above, the profile of fluorescent labels on each imaged labeled region within a DNA molecule is its "signature." By quantifying the amount of label in a labeled region, the sequence of the labeled region can be readily ascertained by comparison to a reference genome, as described further below. When aligned to the reference genome, alterations at the single nucleotide level or more at mapped nick sites within a genome are detectable.

Regardless of whether linearization is required, DNA ligase can be used to remove inherent nicks in the DNA. A DNA ligase reaction with T4 DNA ligase is performed at room temperature overnight. An overnight reaction ensures complete ligation and minimizes residual DNA ligase activity. To further ensure that all inherent nicks are removed, *E. coli* DNA polymerase 1 (10 units) is added with ddNTPs (0.2 µM each) for 30 minutes at 37° C. ddNTPs incorporated into nicks block additional polymerase reaction and avoid random labeling.

A nicking enzyme (e.g., Nb.BbvCI, 20 units, 5'-GC^TGAGG-3'; or Nt.SapI, 20 units, 5'-GCTCTTCN^N-3') is then added with deoxynucleotide triphosphates (dNTPs) and a ddNTP, such as Alexa Fluor 647-aha-dCTP (2 µM), Alexa Fluor 647-aha-dUTP (2 µM), dATP (20 µM), dCTP (1 µM), dGTP (20 µM) or dTTP (1 µM) (all labeled nucleotides available from Invitrogen; Carlsbad, Calif.). The nicking restriction enzyme introduces only single-strand breaks, which therefore allow any cleaved fragments to retain their order. Nicking efficiency, and thus reproducibility, is achieved by optimizing enzyme and DNA concentration, digestion time, buffer composition, temperature and impurities in both enzyme and DNA preparations. Because DNA polymerase is added during endogenous nick blocking, no additional DNA polymerase is added during nick translation. The nick translation reaction is performed for 30 minutes at 37° C. Termination of nick translation defines the other boundary of the neighborhoods and is determined by fluorochrome-fluorochrome steric interactions. Alternatively, nick translation can be terminated by incorporation of a ddNTP, especially when the density of nicking sites is closely spaced. In general, the average length of the bounded region of DNA (i.e., the neighborhood) upon termination by two, consecutively incorporated, fluorochrome-labeled nucleotides is sixty-four bases; whereas the average length of the bounded region of DNA upon termination with a ddNTP is four bases.

EDTA (pH 8.0, 20 µM) is added to quench reactions, and Proteinase K (100 ng/µl) and lauroyl sarcosine (0.1% w/v) are added to remove all enzymes. Because the genomic DNA is not covalently bound to a surface, it is biochemically accessible for these reactions. Following nick translation, DNA is counterstained with YOYO-1 (25 µM; Molecular Probes; Eugene, Oreg.). DNA base pairs to YOYO-1 in a ratio of 6:1 for λ DNA and a ratio of 5:1 to T4 DNA.

Advantageously, the methods described above are performed in a single reaction chamber, meaning that the steps are simply additions, which minimizes transfers that could break the DNA or affect throughput. Remarkably, the information content of the subsequently analyzed labeled regions approaches that of re-sequencing and yields usable information when one nucleotide type is assayed.

Example 2

Quantification of Labeled Nucleotides

Labeled nucleotides incorporated into a labeled region of DNA are quantified. DNA samples containing DNA (1 ng/µl of λ DNA or 0.78 ng/µl of T4 DNA), Tris-EDTA (TE) buffer (pH 8.0), β-mercaptoethanol and POP6 (0.1% w/v; Applied Biosystems; Foster City, Calif.) are loaded onto a surface, such as those described in US Patent Publication No. 2007/0161028, incorporated herein by reference as if set forth in its entirety. TE buffer concentration varies from 1×TE(10 mM Tris and 1 mM EDTA) to 0.01×TE(100 µM Tris and 10 µM EDTA). The ionic strength of the buffer can be varied both before or after entry into the surface to affect elongation of the DNA.

A surface is placed on a microscope-scanner for quantification. One such microscope-scanner is Genome Zephyr, which is an imaging system comprising a fluorescence microscope, stage automation and software. See Zhou S, et al., "A single molecule system for whole genome analysis," in New Methods for DNA Sequencing (K Mitchelson, ed. 2007); and Dimalanta E, et. al., "A microfluidic system for large DNA molecule arrays," Anal. Chem. 76:5293-5301 (2004), each of which is incorporated herein by reference as if set forth in its entirety. The system uses an argon ion, laser-illuminated, inverted Zeiss 135M microscope to image DNA molecules. The microscope is equipped with a 63× Zeiss Plan-Neofluar oil immersion objective, a Dage SIT68GL low-light level video camera connected to a Sony monitor for visual inspection of DNA molecules, and a charge-couple device (CCD) camera for acquiring focus and high-resolution images. A Ludl Electronics x-y stage and focus motor with 0.1-m resolution is used for x-y-z translation. Two emission filters are installed in the microscope, a YOYO-1 emission filter XF3086 and an Alexa Fluor 647 emission filter. The YOYO-1 filter is used to take images of DNA backbones; whereas the Alexa Fluor 647 filter is used to take fluorescence resonance energy transfer (FRET) images. The entire scanning system is under software control by, e.g., ChannelCollect. See Zhou et al., supra and Dimalanta et al., supra.

In the simplest arrangement, the two cameras are identical and the mounting hardware introduces only the following three errors in alignment: (1). the cameras are rotated slightly relative to each other; (2). the cameras are not placed at the precise focal plane leading to a small, but measurable, difference in magnification; and (3). the cameras are offset horizontally/vertically relative to each other.

Under these assumptions, the mapping of image coordinates between images taken with the two cameras can be described by a similarity transformation (i.e., translation, rotation and scale change). The values are calculated by collecting a set of image pairs captured with the two cameras of a target sample with a large number of unique, detailed features. For each image pair, a series of correlations are performed where one image is held constant while the other is rotated and scaled through a variety of angles and magnification factors. In practice, this produces a smooth two-dimensional (rotation vs. magnification) space that can be fit with a parabolic curve. The coordinates of the peak of this curve determine the required rotation and scaling. The average, overall, image pairs are used to refine these numbers. Once the rotation and magnification is calculated, each image pair can be correlated to find the X/Y pixel offsets; these are also averaged to get more precise values.

In practice, however, this process is not sufficient for the purposes described herein. There is also a possibility that each camera may be tilted slightly relative to the focal plane it is placed in. In addition, the cameras may not match exactly. Consequently, a more general affine transformation (i.e., translation, rotation, scaling, and shearing) needs to be calculated. The same set of image pairs used to calculate the similarity transform is used here. For each image pair, one image is held constant while the other is transformed using the previously calculated similarity transform. These images are then subsected using an 8×8 grid, and a correlation is performed between each of the 64 resulting sub-image pairs. The similarity transform is used to minimize the error in these correlations by maximizing the amount of coincident image data in each of the sub-image pairs. This results in a set of 64 X/Y pixel offsets, one for the center of each sub-image pair, spread uniformly across the image space. A set of 64 X/Y pixel offsets is calculated for each of the initial image pairs.

Let:
$C_n=(x,y,1)$ be the homogeneous coordinates of the center of the nth untransformed sub-image Then:
$D_n=(x+dX,y+dY,1)$ are the homogeneous coordinates of the center of the corresponding transformed sub-image.

And solve:

$$D=M*C$$

As a matrix equation using a linear regression technique, the matrix is then combined with the similarity transform to generate the desired affine transformation.

Essentially, the system described above is an adaptation of existing imaging stations outfitted with an emission splitter, housing two filters and CCD cameras. Registration between the two CCD cameras is done by calculating a transform matrix that maps pixel coordinates from one camera to the other, accomplished in two steps. In a first step, a rotation and scaling along with a pixel offset is calculated. In a second step, this transform is refined to compensate for observed variations in horizontal vs. vertical scaling and non-orthogonality of the image axes—using a fixed target on the microscope.

The rotation and scaling are calculated by rotating one of the images, while scaling the companion image and calculating the correlation of these images over a range of angles and magnifications. The angles and magnification where the correlation is near its maximum value are used to estimate the best rotation angle and scale factor. A final correlation is performed on images transformed with this best angle and scale factor for calculating the pixel offset.

There is some drift of the mechanical alignment over time that is a potential source of error. It is possible to use the sub-image alignment technique on the groups of raw images to verify the alignment provided suitable checks are made to ensure only sub-images containing enough correlating information are used.

The system described above generates large image files that are then converted to data, or map files. This is accomplished by machine vision software such as, e.g., Pathfinder. See Zhou et al., supra and Dimalanta et al., supra. Because machine vision software does not match a humans' discernment of objects, such molecular deposition patterns present minimal morphological variation, and this action synergizes image analysis techniques for reliable operation. The masses of a string of restriction fragments determined to originate from the same parental molecule are measured by both integrated fluorescence intensity and apparent length measurements. The end product of this software is a map file, which is then compressed into JPEG format. This ordered restriction map can be thought of as a barcode, and functions as such.

Once the images have been registered, the next step is to remove the green (YOYO-1) signal present in the red (FRET) image due to bandpass of the filters used. Via an algorithm, a threshold is calculated in the green image such that all pixels brighter than this level are known to be in the DNA backbone. The corresponding pixels in the red image are used to calculate a green to red bleed-through ratio at each point. The average of these values is used as the bleed-through factor for a set of images. Each pixel of the red image is adjusted by subtracting the bleed-through factor (~0.025) times the value of the corresponding pixel of the matching green image.

The same threshold-finding algorithm is then applied to the adjusted red, image. Sets of contiguous pixels above the threshold are used to identify punctuates (i.e., visualized nicks that are introduced into the genomic DNA sample by the nicking restriction enzymes). The brightest pixel of each set is used to designate the punctuate location. The punctuates are then correlated with the molecules found in the green images to determine intervals along the DNA backbone.

As a final step, the intensities of the punctuates are calculated. An area around each punctuate is used to determine the background signal present. A Gaussian peak is then fit to the pixels making up each punctuate using a model that includes the system noise. The height and variance of the Gaussian fit is used to calculate the intensity of a punctuate using software and analysis developed for optical sequencing. See Ramanathan et al. (2004), supra.

Maps are read in one of two ways. For example, the map is aligned against a reference genome's map constructed in a computer (i.e., an in silico map). Alternatively, the map is aligned against other single molecule maps or barcodes in the same data set, creating a de novo map. The first type of alignment, however, requires alignment algorithms that consider a most "probable" placement against the reference genome.

The alignment algorithm used herein is a heuristic assembler, which uses a pairwise Smith-Waterman dynamic programming algorithm to subdivide the assembly problem into smaller problems to identify restriction map barcodes. Subsequent computational work for both the alignment and assembly steps is thus distributed over a large network of clustered workstations. See, Valouev A, et al., "Refinement of optical map assemblies," Bioinformatics 22:1217-1224 (2006); Valouev A, et al., "Alignment of optical maps," J. Comput. Biol. 13:442-462 (2006); Zhou et al. (2007), supra; and Zhou S, et al., "Validation of rice genome sequence by optical mapping," BMC Genomics 8:278 (2007).

The algorithm, incorporated into a software program, depends upon a scoring function derived from the likelihood associated with each potential alignment to a reference map, in a manner completely analogous to alignment of DNA or protein sequences. This likelihood function is itself derived from the optical mapping error model and includes terms to account for cut errors. Subsequent computational work for both the alignment and assembly steps is thus distributed over a large network of clustered workstations.

The algorithm is iterative, and the output of each step of the iteration is an approximate map of the genome. In the subsequent step, this approximation is used as the reference map against which all optical maps in a dataset are aligned. Then, optical maps are clustered according to the location of their alignment to the reference genome, such that each cluster is assembled locally. Consensus maps from these assemblies give rise to the reference map for the next step. A human genome assembly used eight iterations, starting with an in silico map derived from the human sequence (NCBI Build 35) as the initial reference. Using this approach, a map of the entire mouse genome was also assembled.

As such, the alignment process not only identifies each molecule, but also reveals structural alterations characterized through common restriction map features including, missing or absent restriction sites, genomic insertions and deletions.

Because one must count the number of co-localized labeled nucleotides, one can then assess the information content of this data compared to the information that one could obtain from fully re-sequencing the same neighborhoods. This information comparison quantifies the notion that counts (i.e., fluorochrome counts) reveal aspects of the underlying sequence instead of the entire sequence, and provides an equivalent to sequence reads of a certain, shorter length.

The following information comparison using statistical entropy was used: $H=\Sigma_x p(x) \log p(x)$, where x is data (from re-sequencing—in one case, and from flash sequencing in the other case), p(x) is the probability associated with the data x, the sum is over all possible realizations of data, and the log p(x) is the base 2 logarithm. Information theory predicts that J has a direct interpretation in terms of information content in data. The amount of information increases with increasing H.

For example, assume that a region of a sample genome ($H_f$, green) equals the same region of a reference genome ($H_r$, red), except for independent point mutations (rate q=1/500 per base) that take the current base uniformly to any of the other three bases. Fluorochrome counting is unable to restore the full sequence in a region. Naturally, there is an information loss, and $H_f < H_r$. This loss become larger as the neighborhood nick site becomes larger. However, the invention produces data with information equal to a significant fraction of that from re-sequencing. Take, for example, a twenty-five base-pair region—knowing base counts instead of sequence corresponds to the information in a fifteen base pair read; knowing only two base counts corresponds to a ten base pair read; and knowing just one count corresponds to a five base pair read.

This invention can also be applied to genomes that have not been sequenced. The methods permit acquisition of sequence information at each of the recognition sites and from the neighborhoods of each recognition site. If a molecule has n recognition sites and the recognition site is composed of m bases, the presence of the labels contributes m*n base-pairs of sequence information. The fluorochrome counts from each neighborhood produce data with additional information equal to a significant fraction of that from de novo sequencing. This additional information is analogous to a representation of base-pair information with IUPAC ambiguity codes.

Two software packages are currently available to provide user interfaces for viewing and interacting with the map data. One is Genspect, and the other is the Santa Cruz Genome Browser with custom Optical Mapping (see Zhou et al. (2007), supra), which provide map data directly linked to public databases, thereby offering sequence data and associated annotation. Links are established to image data within Genspect by clicking on a particular fragment. An Omari image viewer automatically brings up the corresponding set of images for interactive browsing. Users see acquired images of molecules bearing Pathfinder markup annotations, and fragments sizes.

Whole genome scans, also called optical maps, of a human genome result in around 100,000 images. The methods of image processing and analysis described above, reduce such gigabyte-sized files to compact map data files.

The present invention has been described in connection with what are considered to be the most practical and preferred embodiments. However, the invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method for acquiring nucleotide sequence composition information from a DNA molecule, the method comprising the steps of:

introducing a sequence-specific, single-stranded nick site into a DNA molecule; incorporating labeled nucleotides into a region of the DNA molecule extending from the nick site to a termination site at which is incorporated either a ddNTP or at least two consecutive labeled nucleotides;

quantifying the amount of label incorporated into the region of the DNA molecule to ascertain nucleotide sequence composition information about the region; and comparing the amount of label incorporated into the region to the amount expected from the reference genome sequence to determine whether the sequence composition information of the region of the DNA molecule is the same as or different from that of the nucleotide sequence composition information of the corresponding region of the reference genome.

2. The method of claim 1, wherein the nick site is introduced into the DNA by a nicking restriction enzyme.

3. The method of claim 2, wherein the nicking restriction enzyme is selected from the group consisting of Nb.BsmI, Nb.BsrDI, Nb.BtsI, Nb.BbvCI, Nt.AlwI, Nt.BbvCI, Nt.BstNBI, Nt.SapI and Nt.CviPII.

4. The method of claim 1, wherein the labeled nucleotides are incorporated by a polymerase.

5. The method of claim 1, wherein the labeled nucleotides are incorporated by nick translation.

6. The method of claim 1, wherein the termination site is characterized by at least one incorporated labeled nucleotide.

7. The method of claim 1, wherein the termination site is characterized by at least two incorporated labeled nucleotides.

8. The method of claim 1, wherein the termination site is characterized by a terminator.

9. The method of claim 8, wherein the terminator is selected from an incorporated dideoxynucleotide or by an incorporated dideoxynucleotide and dye.

10. The method of claim 1, further including the step of reducing or preventing incorporation of label from non-sequence-specific, endogenous nick sites in the DNA molecule before the introducing step.

11. The method of claim 10, wherein the step of reducing or preventing incorporation of label is selected from the group of steps consisting of repairing endogenous nicks in the DNA molecule and blocking endogenous nicks in the DNA molecule.

12. The method of claim 1, further including the step of tagging the DNA molecule with a labeled molecule outside the region of the DNA molecule.

13. The method of claim 12, wherein the labeled molecule is a globally staining fluorochrome.

14. The method of claim 13, wherein the globally staining fluorochrome is YOYO-1.

15. The method of claim 1, further including the step of removing protein from the DNA molecule.

16. The method of claim 1, wherein the labeled nucleotides are selected from Alexa-labeled nucleotides and Cy5-labeled nucleotides.

17. A method for estimating nucleotide sequence composition information from a DNA molecule, the method comprising the steps of:
   introducing a sequence-specific, single-stranded nick site into a DNA molecule; incorporating labeled nucleotides into a region of the DNA molecule extending from the nick site to a termination site at which is incorporated either a ddNTP or at least two consecutive labeled nucleotides;
   quantifying the amount of label incorporated into the region to estimate nucleotide sequence composition information about the region.

18. The method of claim 17, wherein the nick site is introduced into the DNA by a nicking restriction enzyme.

19. The method of claim 18, wherein the nicking restriction enzyme is selected from the group consisting of Nb.BsmI, Nb.BsrDI, Nb.BtsI, Nb.BbvCI, Nt.AlwI, Nt.BbvCI, Nt.BstNBI, Nt.SapI and Nt.CviPII.

20. The method of claim 17, wherein the labeled nucleotides are incorporated by a polymerase.

21. The method of claim 17, wherein the labeled nucleotides are incorporated by nick translation.

22. The method of claim 17, wherein the termination site is characterized by at least one incorporated labeled nucleotide.

23. The method of claim 17, wherein the termination site is characterized by at least two incorporated labeled nucleotides.

24. The method of claim 17, wherein the termination site is characterized by a terminator.

25. The method of claim 24, wherein the terminator is selected from an incorporated dideoxynucleotide or by an incorporated dideoxynucleotide and dye.

26. The method of claim 17, further including the step of reducing or preventing incorporation of label from non-sequence-specific, endogenous nick sites in the DNA molecule before the introducing step.

27. The method of claim 26, wherein the step of reducing or preventing incorporation of label is selected from the group of steps consisting of repairing endogenous nicks in the DNA molecule and blocking endogenous nicks in the DNA molecule.

28. The method of claim 17, further including the step of tagging the DNA molecule with a labeled molecule outside the region of the DNA molecule.

29. The method of claim 28, wherein the labeled molecule is a globally staining fluorochrome.

30. The method of claim 29, wherein the globally staining fluorochrome is YOYO-1.

31. The method of claim 17, further including the step of removing protein from the DNA molecule.

32. The method of claim 17, wherein the labeled nucleotides are selected from Alexa-labeled nucleotides and Cy5-labeled nucleotides.

* * * * *